(12) United States Patent
Long et al.

(10) Patent No.: US 12,324,915 B2
(45) Date of Patent: *Jun. 10, 2025

(54) INNER EAR ELECTRODE IMPLANTATION OUTCOME ASSESSMENT

(71) Applicant: Cochlear Limited, Macquarie University (AU)

(72) Inventors: Christopher Joseph Long, Centennial, CO (US); Zachary Mark Smith, Pymble (AU); Paul Michael Carter, Galson (AU); Peter Gibson, South Coogee (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/171,892

(22) Filed: Feb. 21, 2023

(65) Prior Publication Data

US 2023/0271009 A1 Aug. 31, 2023

Related U.S. Application Data

(63) Continuation of application No. 16/392,739, filed on Apr. 24, 2019, now Pat. No. 11,612,745.

(60) Provisional application No. 62/661,703, filed on Apr. 24, 2018.

(51) Int. Cl.
| | |
|---|---|
| *A61N 1/36* | (2006.01) |
| *A61N 1/02* | (2006.01) |
| *A61N 1/05* | (2006.01) |
| *H04R 25/00* | (2006.01) |
| *A61B 5/00* | (2006.01) |

(52) U.S. Cl.
CPC ......... *A61N 1/36039* (2017.08); *A61N 1/025* (2013.01); *A61N 1/0541* (2013.01); *H04R 25/50* (2013.01); *H04R 25/70* (2013.01); *A61B 5/6815* (2013.01)

(58) Field of Classification Search
CPC .... A61B 5/6815; A61N 1/025; A61N 1/0541; A61N 1/36039; H04R 25/50; H04R 25/70
See application file for complete search history.

(56) References Cited

U.S. PATENT DOCUMENTS

| | | |
|---|---|---|
| 4,261,372 A | 4/1981 | Hansen et al. |
| 5,922,017 A | 7/1999 | Bredberg et al. |
| 6,074,422 A | 6/2000 | Berrang et al. |
| 6,487,453 B1 | 11/2002 | Kuzma et al. |
| 6,498,954 B1 | 12/2002 | Kuzma et al. |
| 8,150,528 B2 | 4/2012 | Jolly |

(Continued)

FOREIGN PATENT DOCUMENTS

| | | |
|---|---|---|
| AU | 722310 A | 10/1997 |
| WO | 2016126900 A1 | 8/2016 |

OTHER PUBLICATIONS

Baumann et al., The Cochlear Implant Electrode-Pitch Function, Hearing Research 213.1-2 (2006): 34-42, 9 pages.

(Continued)

*Primary Examiner* — Jon Eric C Morales
(74) *Attorney, Agent, or Firm* — Edell, Shapiro & Finnan, LLC

(57) ABSTRACT

Presented herein are techniques for assessing one or more outcomes associated with implantation of one or more electrodes into the inner ear of a recipient.

21 Claims, 14 Drawing Sheets

(56) References Cited

U.S. PATENT DOCUMENTS

| | | | |
|---|---|---|---|
| 11,612,745 B2* | 3/2023 | Long | A61N 1/0541 607/137 |
| 2008/0154339 A1* | 6/2008 | Carter | A61N 1/0541 607/57 |
| 2010/0331913 A1 | 12/2010 | Mann et al. | |
| 2015/0314122 A1* | 11/2015 | Kabot | A61N 1/08 607/137 |

OTHER PUBLICATIONS

Chouard et al., Long-Term Results of the Multichannel Cochlear Implant, Annals of the New York Academy of Sciences 405.1 (1983): pp. 387-411.

Wess et al., The Effect of Interaural Mismatches on Contralateral Unmasking with Single-Sided Vocoders, Ear & Hearing 2017; vol. 38; No. 3, pp. 374-386.

Montandon et al., Ineraid Cochlear Implant in the Ossified Cochlea: Surgical Techniques and Results, The American Journal of Otology, vol. 15, No. 6, Nov. 1994, pp. 748-751.

Middlebrooks et al., Selective Electrical Stimulation of the Auditory nerve Activates a Pathway Specialized for High Temporal Acuity, The Journal of Neuroscience, Feb. 3, 2010, 30(5), pp. 1937-1946.

Kileny et al., Performance With the 20 + 2L Lateral Wall Cochlear Implant, The American Journal of Otology, vol. 19, No. 3, 1998, pp. 313-319.

* cited by examiner

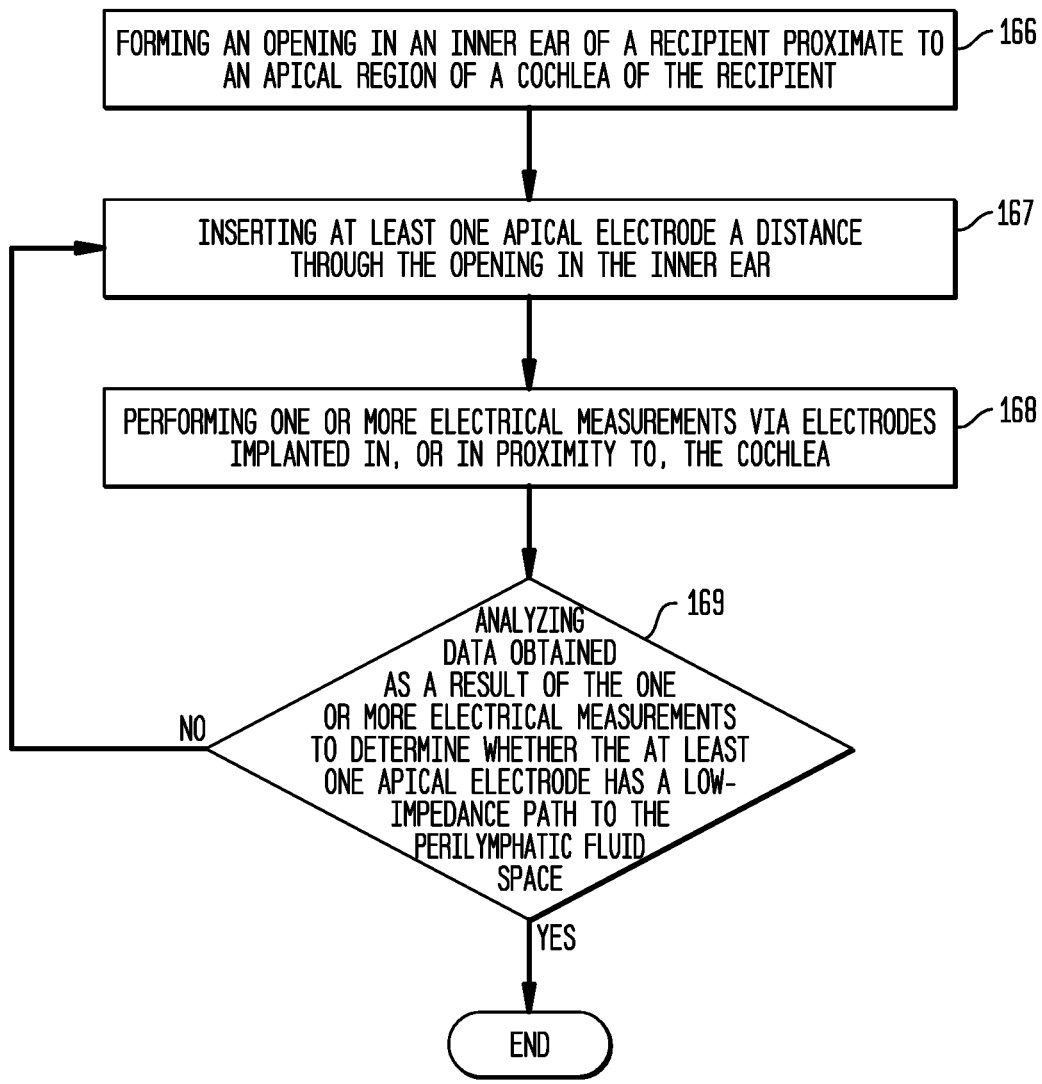

CADAVER SPECIMEN #2

CADAVER SPECIMEN #1

CADAVER SPECIMEN #1

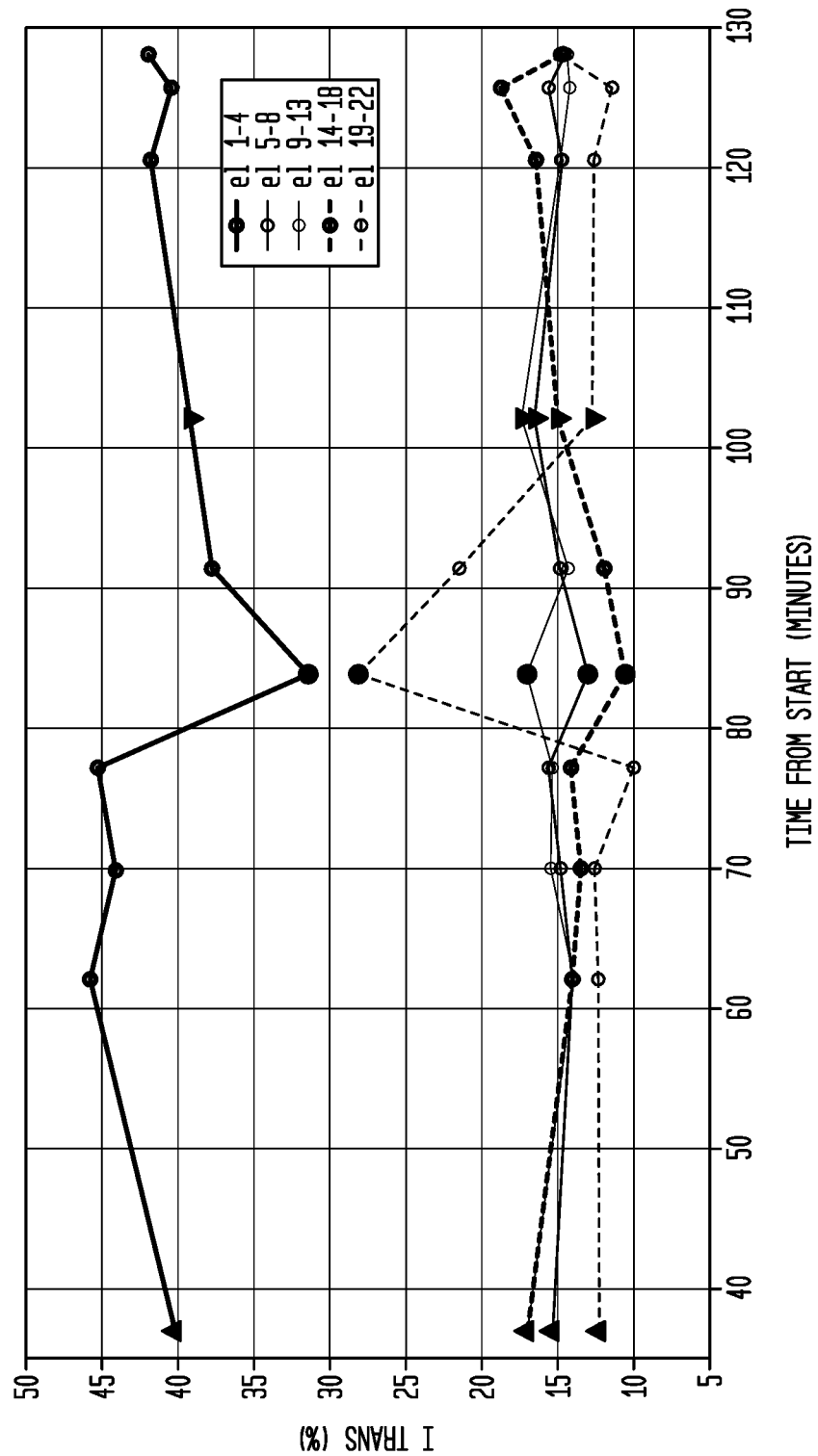

| | |
|---|---|
| PERFORMING ONE OR MORE INITIAL ELECTRICAL MEASUREMENTS BETWEEN AN APICAL ELECTRODE POSITIONED IN A RECIPIENT'S COCHLEA VIA AN APICAL COCHLEOSTOMY AND AN EXTRA-COCHLEAR ELECTRODE | 191 |
| SEALING THE APICAL COCHLEOSTOMY | 192 |
| PERFORMING ONE OR MORE ADDITIONAL ELECTRICAL MEASUREMENTS BETWEEN THE APICAL ELECTRODE AND THE EXTRA-COCHLEAR ELECTRODE | 193 |
| ANALYZING THE RESULTS OF THE ONE OR MORE INITIAL ELECTRICAL MEASUREMENTS AND/OR THE RESULTS OF THE ONE OR MORE ADDITIONAL ELECTRICAL MEASUREMENTS | 194 |

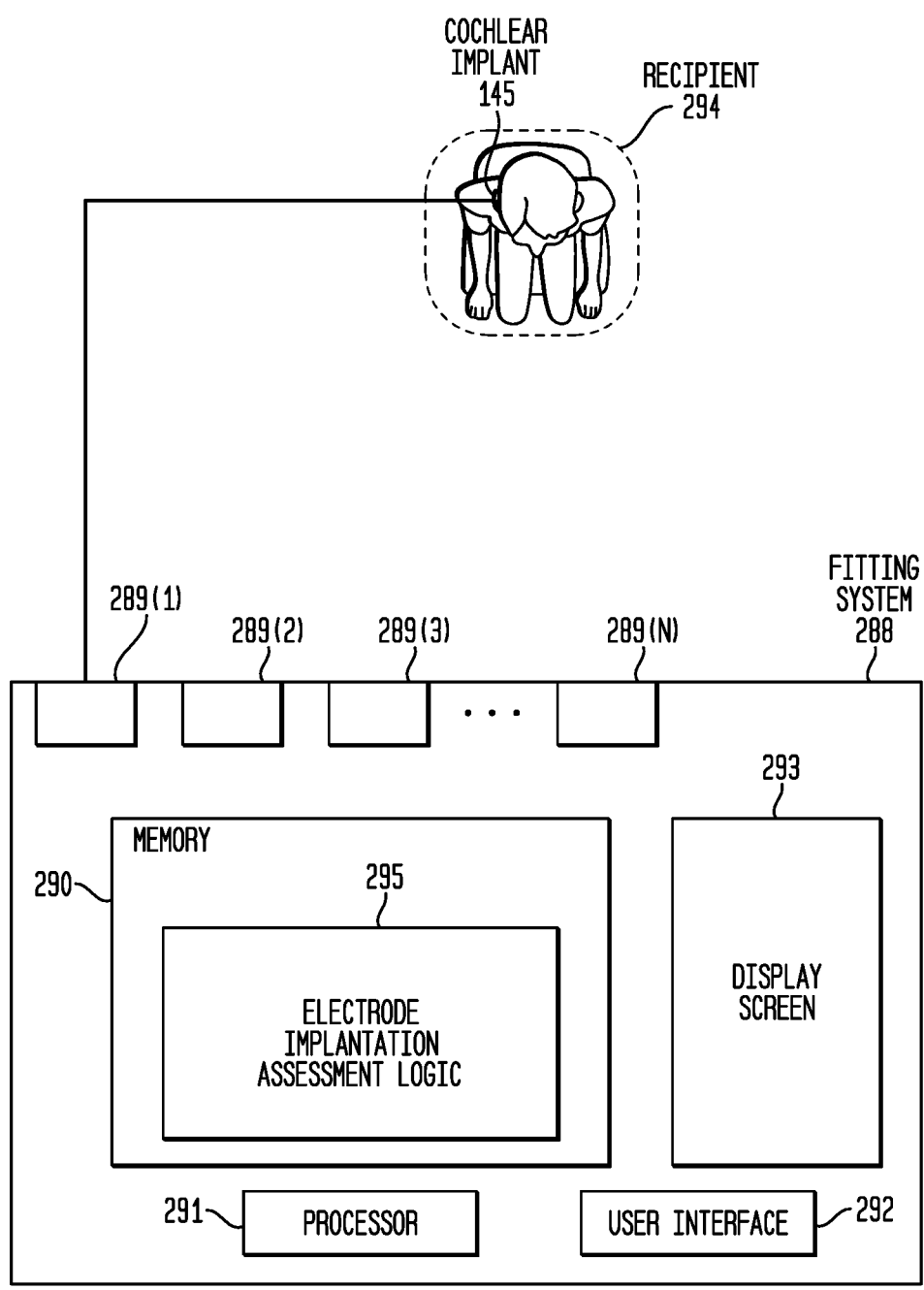

INNER EAR ELECTRODE IMPLANTATION OUTCOME ASSESSMENT

CROSS-REFERENCE TO RELATED APPLICATIONS

This application is a continuation of U.S. application Ser. No. 16/392,739, filed Apr. 24, 2019, which claims the benefit of U.S. Provisional Patent Application No. 62/661,703, filed on Apr. 24, 2018, the contents of which is hereby incorporated by reference herein.

BACKGROUND

Field of the Invention

The present invention generally relates to assessment of outcomes relating to implantation of one or more electrodes into the inner ear of a recipient.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

SUMMARY

In one aspect, a method is provided. The method comprises: forming an opening in an inner ear of a recipient proximate to an apical region of a cochlea of the recipient: inserting at least one apical electrode through the opening in the inner ear; performing one or more electrical measurements via electrodes implanted in, or in proximity to, the cochlea; and analyzing data obtained as a result of the one or more electrical measurements to determine whether the at least one apical electrode has a low-impedance path to a perilymphatic fluid space of the cochlea.

In another aspect, a method is provided. The method comprises: inserting one or more electrodes through an opening formed in the inner ear of a recipient: following insertion of the one or more electrodes through the opening in the inner ear, sealing the opening formed in the inner ear: performing one or more electrical measurements via the one or more electrodes inserted into the inner ear and at least one extra-cochlear electrode positioned outside of the inner ear; and analyzing data obtained as a result of the one or more electrical measurements to determine whether the opening in the inner ear is electrically sealed.

In another aspect, a system is provided. The system comprises: a basilar cochlea electrode assembly comprising a plurality of intra-cochlea electrodes, wherein the basilar cochlea electrode assembly is configured to be inserted into a cochlea of a recipient via a basal region of the cochlea: one or more apical electrodes configured to be inserted into an apical region of the cochlea: a stimulation unit configured to deliver current signals to the cochlea using one or more of the plurality of intra-cochlea electrodes or at least one of the one or more apical electrodes and perform one or more electrical measurements in response to delivery of the current signals; and one or more processors configured to, based on results of the one or more electrical measurements, determine whether the one or more apical electrodes are in electrical contact with a perilymphatic fluid space of the cochlea.

BRIEF DESCRIPTION OF THE DRAWINGS

Embodiments of the present invention are described herein in conjunction with the accompanying drawings, in which:

FIG. 3 is a flowchart illustrating a method, in accordance with certain embodiments presented herein:

FIG. 8B is a graph illustrating Summed Transverse currents through groups of electrodes implanted in a second cochlear cadaver specimen, in accordance with certain embodiments presented herein;

FIG. 10 is a flowchart illustrating a method, in accordance with certain embodiments presented herein:

FIG. 12 is a schematic diagram illustrating a system configured to implement certain techniques presented herein.

DETAILED DESCRIPTION

Presented herein are techniques for assessing one or more outcomes associated with implantation of one or more electrodes into the inner ear of a recipient. In accordance with certain embodiments, the techniques presented herein may be utilized to assess outcomes associated with implantation of one or more electrodes into the apical region of a cochlea of a recipient.

As noted, the techniques presented herein may be utilized to assess outcomes for implantation of one or more electrodes into various areas of a recipient's inner ear, such as the cochlea, the vestibular system, etc. However, merely for ease of illustration, the techniques presented herein are primarily described with reference to implantation of an electrode into the apical region of a cochlea of a cochlear implant recipient. For ease of description, an electrode implanted in, or configured to be implanted in, the apical region of a cochlea of a cochlear implant recipient is referred to herein as an "apical cochlea electrode" or, more simply, an "apical electrode."

Before describing details of the techniques presented herein, relevant aspects of an example cochlea 140 in which an apical electrode may be implanted are first described below with reference to FIGS. 1A-1B. More specifically, FIG. 1A is a perspective view of the cochlea 140 partially cut-away to display the canals and nerve fibers of the cochlea, while FIG. 1B is a cross-sectional view of one turn of the canals of the cochlea 140.

Figure 1A:
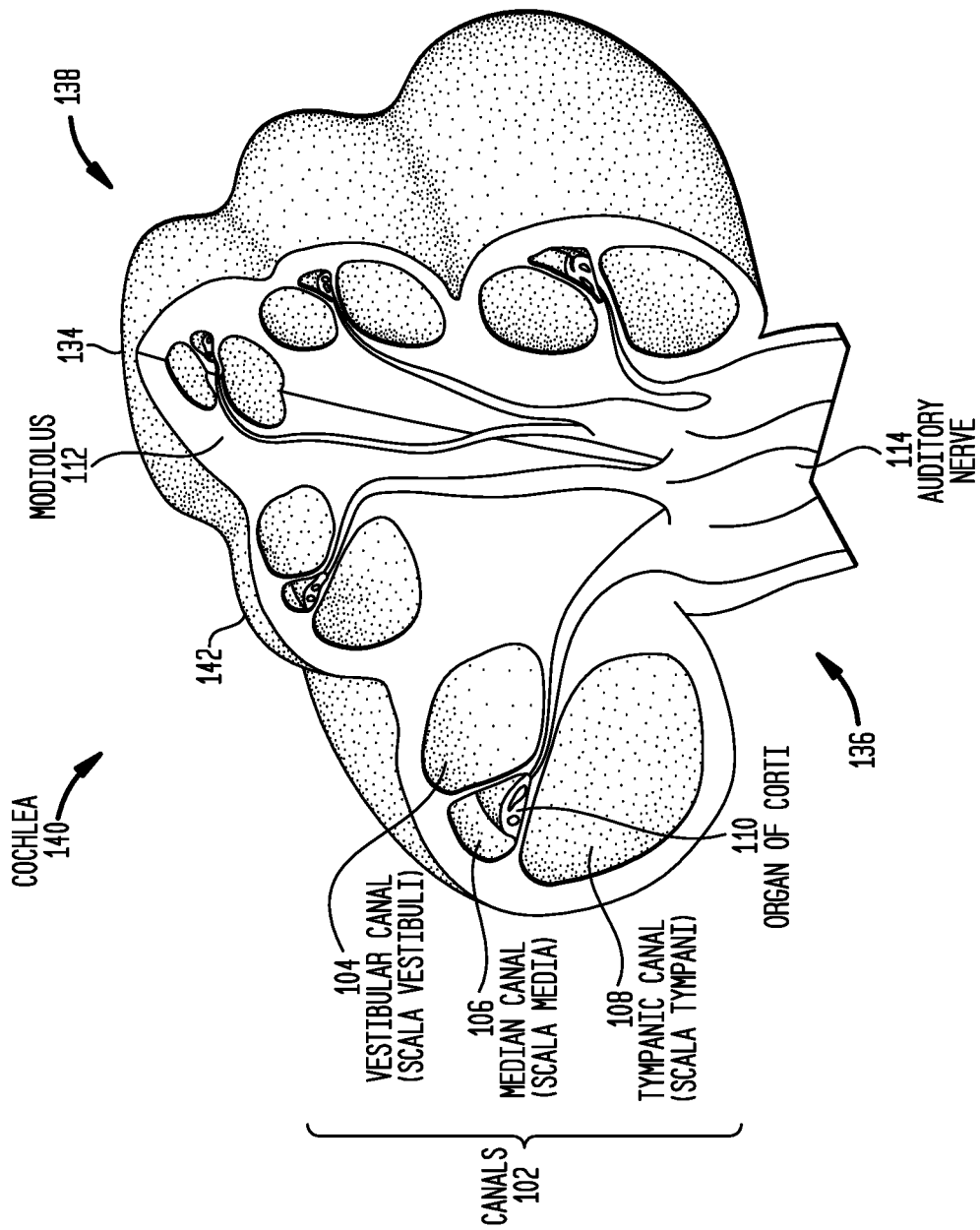
FIG. 1A is a partially cut-away, perspective view of a cochlea in which an apical cochlea electrode assembly can be implanted.
Figure 1B:
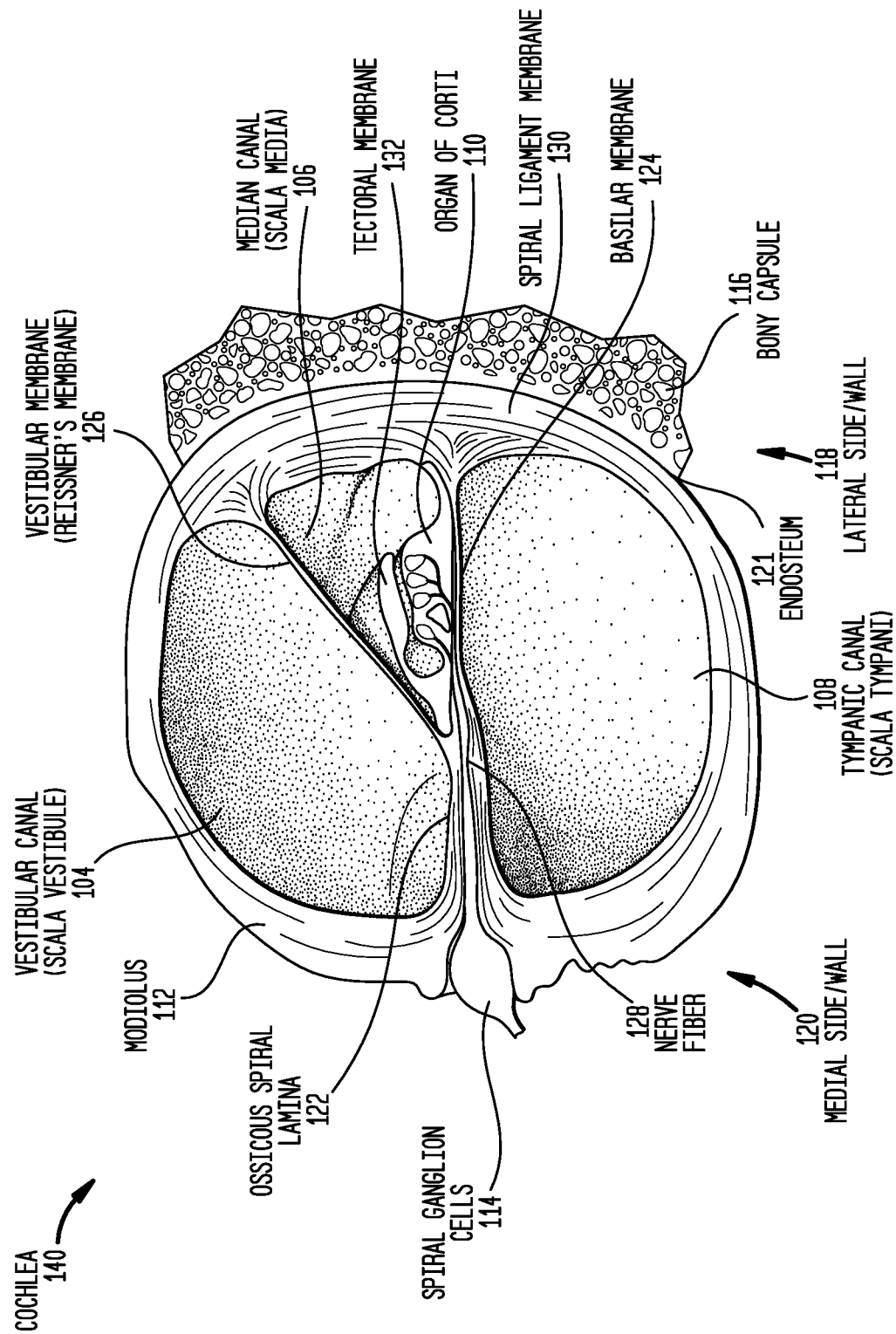
FIG. 1B is a cross-sectional view of one turn of the canals of the cochlea of FIG. 1A.

Referring first to FIG. 1A, cochlea 140 is a conical spiral structure comprising three parallel fluid-filled canals or ducts, collectively and generally referred to herein as canals 102. Canals 102 comprise the tympanic canal 108, also referred to as the scala tympani 108, the vestibular canal 104, also referred to as the scala vestibuli 104, and the median canal 106, also referred to as the scala media 106. Cochlea 140 spirals about modiolus 112 several times and terminates at cochlea apex 134.

Portions of cochlea 140 are encased in a bony labyrinth/capsule 116 and the endosteum 121 (e.g., a thin vascular membrane of connective tissue that lines the inner surface of the bony tissue that forms the medullary cavity of the bony labyrinth). Spiral ganglion cells 114 reside on the opposing medial side 120 (the left side as illustrated in FIG. 1B) of cochlea 140. A spiral ligament membrane 130 is located between lateral side 118 of spiral tympani 108 and bony capsule 116, and between lateral side 118 of scala media 106 and bony capsule 116. Spiral ligament 130 also typically extends around at least a portion of lateral side 118 of scala vestibuli 104.

The fluid in the tympanic canal 108 and the vestibular canal 104, referred to as perilymph, has different properties than that of the fluid which fills scala media 106 and which surrounds organ of Corti 110, referred to as endolymph. The tympanic canal 108 and the vestibular canal 104 collectively form the perilymphatic fluid space 109 of the cochlea 140. Sound entering a recipient's auricle (not shown) causes pressure changes in cochlea 140 to travel through the fluid-filled tympanic and vestibular canals 108, 104. As noted, the organ of Corti 110 is situated on basilar membrane 124 in the scala media 106 and contains rows of 16,000-20,000 hair cells (not shown) which protrude from its surface. Above them is the tectoral membrane 132 which moves in response to pressure variations in the fluid-filled tympanic and vestibular canals 108, 104. Small relative movements of the layers of membrane 132 are sufficient to cause the hair cells in the endolymph to move thereby causing the creation of a voltage pulse or action potential which travels along the associated nerve fiber 128. Nerve fibers 128, embedded within the spiral lamina 122, connect the hair cells with the spiral ganglion cells 114 which form auditory nerve 114. Auditory nerve 114 relays the impulses to the auditory areas of the brain (not shown) for processing.

The place along basilar membrane 124 where maximum excitation of the hair cells occurs determines the perception of pitch and loudness according to the place theory. Due to this anatomical arrangement, cochlea 140 has characteristically been referred to as being "tonotopically mapped." That is, regions of cochlea 140 toward basal region 136 are responsive to high frequency signals, while regions of cochlea 140 toward apical region 138 are responsive to low frequency signals. These tonotopical properties of cochlea 140 are exploited in a cochlear implant by delivering stimulation signals within a predetermined frequency range to a region of the cochlea that is most sensitive to that particular frequency range.

In general, the basal region 136 is the portion of the cochlea 140 located closest to the stapes (not shown in FIGS. 1A and 1B) and extends to approximately the first turn of the cochlea (i.e., the region of the cochlea 140 between the cochlea openings, including the round and oval windows, the first cochlea turn). The apical region 138 is portion of the cochlea 140 in proximity to the cochlear apex 134. More specifically, the cochlea 140 is generally a conical spiral structure (i.e., the spiral-like shape) and the apical region 138 of the cochlea 140 is generally the last/final (i.e., most apical) 360 degrees of the cochlea and encompasses the cochlea areas tonotopically associated with frequencies below 1000 Hz.

Figure 2:
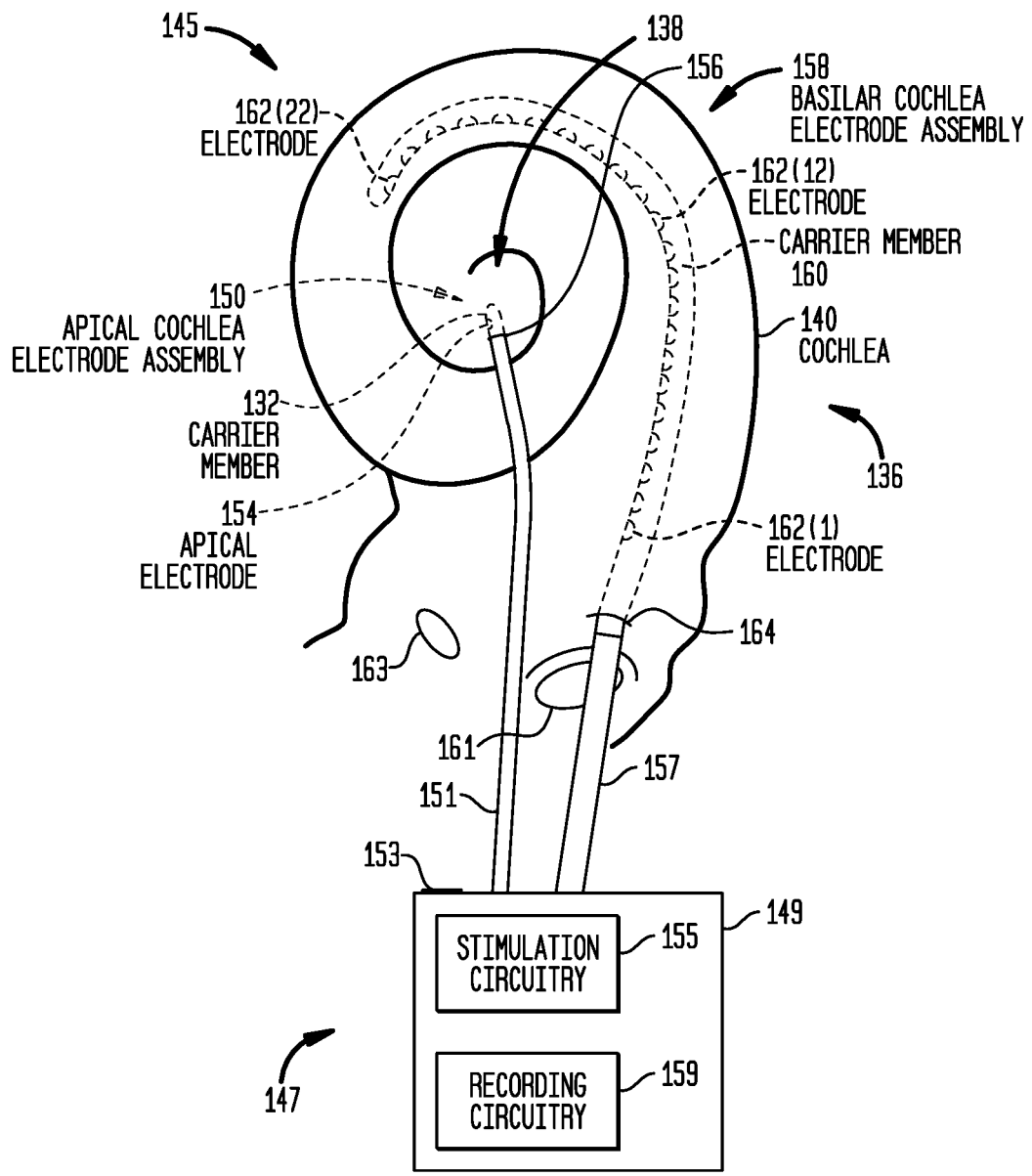
FIG. 2 is a schematic diagram illustrating an apical cochlea electrode assembly and a basilar cochlea electrode assembly implanted in a cochlea of a recipient, in accordance with certain embodiments presented herein.

FIG. 2 is a schematic diagram illustrating the implantation of an apical electrode into a cochlea of a recipient. For ease of illustration, FIG. 2 will be described with reference to implantation of a single apical electrode 154 into the apical region 138 of cochlea 140 of FIGS. 1A and 1B. It is to be appreciated that the implantation of a single apical electrode is illustrative and that the techniques presented herein may be utilized to assess outcomes associated with implantation of one or multiple apical electrodes into the cochlea and/or to assess outcomes associated with implantation of one or multiple electrodes into other portions of a recipient's inner ear.

In the specific example of FIG. 2, the apical electrode 154 is disposed in a carrier member 152 (e.g., a flexible silicone body) and the apical electrode 154 is electrically connected to an implanted stimulation unit 147 via one or more wires (not shown in FIG. 2) extending through a lead 151. The apical electrode 154 and the carrier member 152 are sometimes collectively referred to herein as an "apical cochlea electrode assembly" 150. The apical electrode 154 inserted into cochlea 140 via an apical cochleostomy 156. As used herein, cochleostomy is a surgically formed opening formed in the outer wall 142 (FIG. 1A) of cochlea 140.

FIG. 2 also illustrates a basilar cochlea electrode assembly 158 implanted in cochlea 140. A basilar cochlea electrode assembly, such as basilar cochlea electrode assembly 158, is at least comprised of one or more electrodes that are configured to be inserted into the cochlea 140 via the basal region 136. That is, a basilar cochlea electrode assembly may be inserted into and/or through the basal region of a recipient's cochlea. In the specific embodiment of FIG. 2, the basilar cochlea electrode assembly 158 comprises a carrier member 160 and twenty-two (22) intra-cochlea electrodes 162, sometimes referred to individually as intra-cochlea electrodes 162(1)-162(22). The intra-cochlea electrodes 162(1)-162(22) are electrically connected to the stimulation unit 147 via one or more wires (not shown in FIG. 2) extending through a lead 157.

The basilar cochlea electrode assembly 158 is shown inserted into cochlea 140 via a basal cochleostomy 164. However, it is to be appreciated that the basilar cochlea electrode assembly 158 could also be inserted through the round window 161 or the oval window 163.

Also shown in FIG. 2 is an extra-cochlear electrode (ECE) 153. In this example, the extra-cochlear electrode 153 is disposed on the housing (can) 149 of the stimulation unit 147 (i.e., outside of the recipient's cochlea 140). However, the extra-cochlear electrode 153 could alternatively be configured to be implanted in the recipient adjacent to the cochlea 140, but not within the cochlea 140.

The stimulation unit 147 includes stimulation circuitry 155 that is configured to generate stimulation (current) signals for delivery to the recipient via, for example, one or more of the apical electrode 154, intra-cochlea electrodes 162(1)-162(22), etc. The stimulation signals electrically stimulate the recipient's auditory nerve cells in a manner that causes the recipient to perceive captured/received audio signals. The stimulation unit 147 includes recording circuitry 159 that is configured to perform electrical measurements via electrodes implanted in, or in proximity to, the cochlea 140, such as via apical electrode 154, intra-cochlea electrodes 162(1)-162(22), and extra-cochlear electrode 153. The results of these electrical measurements may be provided to one or more external components (e.g., a fitting system such as that shown in FIG. 12) for subsequent analysis and, ultimately, assessment of one or more outcomes associated with implantation of the apical electrode 154 into the cochlea 140.

Apical cochlea electrode assembly 150, basilar cochlea electrode assembly 158, and stimulation module 147 are sometimes collectively and generally referred to herein as an "apical cochlear implant" 145. Although not shown in FIG. 2 for ease of description, the apical cochlear implant 145 may include other components (e.g., sound inputs, sound processor, etc.) that enable the cochlear implant 145 to receive sound signals and convert the received sound signals into stimulation signals for delivery to cochlea 140. These components may be included in stimulation unit 147, included in a separate implanted module, and/or included in an external component that is configured for transcutaneous communication with the stimulation module.

Cochlear implants have been used successfully for many years to treat sensorineural hearing loss. A basilar cochlea electrode assembly is inserted into a recipient's cochlea via an opening in the basal region of the cochlea and extends some distance into the cochlea therefrom. Different lengths of basilar cochlea electrode assemblies have been proposed and implanted in recipients, thus the insertion distance of basilar cochlea electrode assemblies can vary. However, due at least in part of the conical spiral structure of the cochlea (i.e., the spiral-like shape) and the delicate anatomical structure of the cochlea, all basilar cochlea electrode assemblies have a maximum insertion distance in which the most distal electrodes are well short of the apical region of the cochlea. As a result, basilar cochlea electrode assemblies generally stimulate higher frequency tonotopic regions of the cochlea (e.g., auditory nerve fibers). However, the tonotopic regions of the cochlea response to lower frequencies, such as frequencies below one (1) kHz are believed to have the best temporal precision. As such, this lower frequency region would be expected to represent information in difficult listening situations, such as speech in noise, music, etc. and may capture binaural timing cues better than higher frequency regions. Lack of access to these low-frequency regions in traditional cochlear implants may contribute to common problems with traditional cochlear implants, such as difficulty with speech in noise, music perception, and binaural timing perception, and frequency-shifted perception of sounds.

The arrangement shown in FIG. 2 illustrates an enhancement to traditional cochlear implants in that the apical electrode 154 provides the ability to directly stimulate the apical region 138 of the cochlea and, accordingly, the tonotopic regions of the cochlea 140) responsive to low frequencies (e.g., frequencies below 1 kHz). In the arrangement of FIG. 2, the stimulation provided by apical electrode 154 can complement stimulation from the intra-cochlea electrodes 162(1)-162(22), at the tonotopic regions of the cochlea 140 responsive to higher frequencies.

Various factors may contribute to a successful use of the apical electrodes to stimulate the tonotopic regions of a cochlea responsive to low frequencies. Presented herein are techniques that enable a user, such as a surgeon, to intraoperatively assess, and potentially optimize, outcomes associated with insertion of apical electrodes, such as apical electrode 154 of apical cochlea electrode assembly 150, into the cochlea of a recipient. More specifically, in certain embodiments the techniques presented herein may be used to electrically guide insertion of cochlea electrode(s) into the apical region of a recipient's cochlea. The techniques presented herein may also or alternatively, in certain embodiments, be used to confirm an appropriate cochleostomy seal following insertion of cochlea electrode(s). In addition, the techniques may also or alternatively be used to, in certain embodiments, optimize the implanted location of cochlea electrode(s). Further features of the techniques presented herein are provided below.

Referring first to FIG. 3, shown is a method 165 that makes use of electrical measurements, such as generalized impedance measurements, Electrode Voltage Tomography (EVT) measurements, neural response measurements, etc. to guide implantation of at least one apical electrode into the apical region of a recipient's cochlea. For ease of illustration, method 165 will be described with reference to implantation of apical electrode 154 into apical region 138 of cochlea 140, as described above with reference to FIG. 2.

More specifically, method 165 begins at 166 where a procedure is performed to form an opening in the inner ear of the recipient proximate to the apical region 138 of the cochlea 140 to provide access to an apical region 138 of the cochlea. In certain examples, forming opening in the inner ear may include forming an opening in the bony labyrinth/capsule 116 surrounding the inner ear. In other embodiments, forming opening in the inner ear may include forming an opening in the bony labyrinth 116 as well as forming an opening in the endosteum 121 (e.g., forming a cochleostomy). A cochleostomy formed proximate to the apical region 138 of the cochlea is sometimes referred to herein as an apical cochleostomy. In FIG. 2, above, apical cochlea electrode assembly 150 is inserted through an apical cochleostomy 156 (i.e., an opening formed through the bony labyrinth 116 and the endosteum 121).

Returning to FIG. 2, at 167, the apical electrode 154 is inserted a distance through the opening in the inner ear (e.g., inserted a distance through apical cochleostomy 156). At 168, one or more electrical measurements are performed via electrodes implanted in, or in proximity to, the cochlea 140. At 169, data captured as a result of the electrical measurements is analyzed to determine whether apical electrode 154 has a low-impedance path to the perilymphatic fluid 109 (e.g., is in electrical contact with the perilymphatic fluid space) of the cochlea 148. In certain embodiments, electrical contact with the perilymphatic fluid space 109 may refer to stable physical contact between the apical electrode 154 and the perilymph within the cochlea 140 or stable physical contact between the apical electrode 154 and the endosteum of the cochlea 140.

If it is determined at 169 that the apical electrode 154 has a low-impedance path to the perilymphatic fluid space 109 of the cochlea 140, then method 165 may be terminated. However, if apical electrode 154 does not have a low-impedance path to the perilymphatic fluid space 109, then the operations at 167, 168, and 169 may be repeated until it is determined that the apical electrode 154 does have a low-impedance path to the perilymphatic fluid space 109.

As noted above, the apical electrode 154 may be used with basilar cochlea electrode assembly 158. In certain embodiments, prior to implantation of the apical electrode 154 into the apical region 138, the basilar cochlea electrode assembly 158 may be first inserted into cochlea 140. The intra-cochlea electrodes 162(1)-162(22), possibly in combination with apical electrode 154 and/or one or more other electrodes, such as extra-cochlea electrode 153, may be used to perform the electrical measurements at 168.

In accordance with the techniques presented herein, the electrical measurements performed at 168 and the analysis at 169 may each take a number of different forms. In some embodiments, the electrical measurements at 168 and the analysis at 169 are performed to determine whether there is a selected pattern (e.g., direction, amount, etc.) of current flow towards (e.g., in the direction of) the cochlea apex 134. More specifically, it has been discovered that, in arrangements that include only a basilar cochlea electrode assembly, generally only a limited amount of the current delivered via the basilar cochlea electrode assembly exits the cochlea via the apical region. Therefore, in the arrangement of FIG. 2 that includes apical electrode 154 and the intra-cochlea electrodes 162(1)-162(22), a determination that there is a selected pattern of current flow towards the cochlea apex 134 indicates that the apical electrode 154 has a low-impedance path to the perilymphatic fluid space 109 (i.e., current would not flow in that manner without the apical electrode 154 drawing the current thereto).

In certain embodiments, the determination of a selected pattern of current flow towards the cochlea apex 134 is a determination that there is an increased current flow, relative to a baseline pattern of current flow. In one example, the baseline pattern of current flow is determined using the results of one or more voltage or impedance measurements performed/obtained prior to insertion of the apical electrode 154 through the opening in the inner ear (e.g., apical cochleostomy 156). Alternative, the baseline pattern of current flow is determined using normative data. In other embodiments, the determination of a selected amount of current flow towards the cochlea apex 134 is a determination that the detected current flow exceeds a predetermined threshold.

In some embodiments, impedance measurements may be performed between the apical electrode 154 and one or more of the intra-cochlea electrodes 162(1)-162(22). In certain such embodiments, the data captured through the impedance measurements (e.g., impedance values) may be analyzed relative to impedance measurements made before insertion of the apical electrode 154 into the cochlea 140, predetermined normative measurements, or some other baseline measure. In other examples, data captured through the impedance measurements may be analyzed to identify a change in current exiting at each location along the cochlea.

In certain embodiments, the impedance measurements may be performed between the apical electrode 154 and a selected one of the intra-cochlea electrodes 162(1)-162(22). In other embodiments, two or more of the intra-cochlea electrodes 162(1)-162(22) may be electrically connected with one another (e.g., commoned together) in order to perform the impedance measurements. Implementations using some or all the intra-cochlea electrodes combined together (either during the measurement or afterward in analysis) for the impedance measurement increases the sensitivity of the impedance measurements, relative to the use of a single intra-cochlea electrode, which in turn facilitates the determination of whether the apical electrode 154 is in contact with the perilymphatic fluid space 109.

Alternatively or additionally, Electrode Voltage Tomography (EVT) measurements and/or Neural Response Telemetry (NRT) measurements may be performed. Different EVT measurements can be observed when the apical electrode 154 is placed in the apical region 138 of the cochlea 140 than when the apical electrode is outside the cochlea. For example, one possible implementation of the analysis would be to identify a change current flow paths at locations apical to the intra-cochlear electrodes 162(1)-162(22). In one example, the EVT measurements use the intra-cochlear electrodes 162(1)-162(22) as active stimulating and active recording electrodes, use the apical electrode 154 as a stimulation reference, and use as extra-cochlear electrode, such as extra-cochlear electrode 153, as a recording reference.

The cochlear fluid has resistivity and, as such, with the EVT measurements, the measured voltage decreases with distance. There is a specific pattern with a normal insertion of a basilar cochlear electrode array and differences can be observed when an apical return point is provided by apical electrode 154 in contact with the perilymphatic fluid space 109 (e.g., a change in current flow where more current ends up heading towards the apex 134, which is normally not an exit point for current in conventional basilar electrode array insertion). This is generally shown in FIGS. 4A-4C and 5A-5C.

Figure 4A:
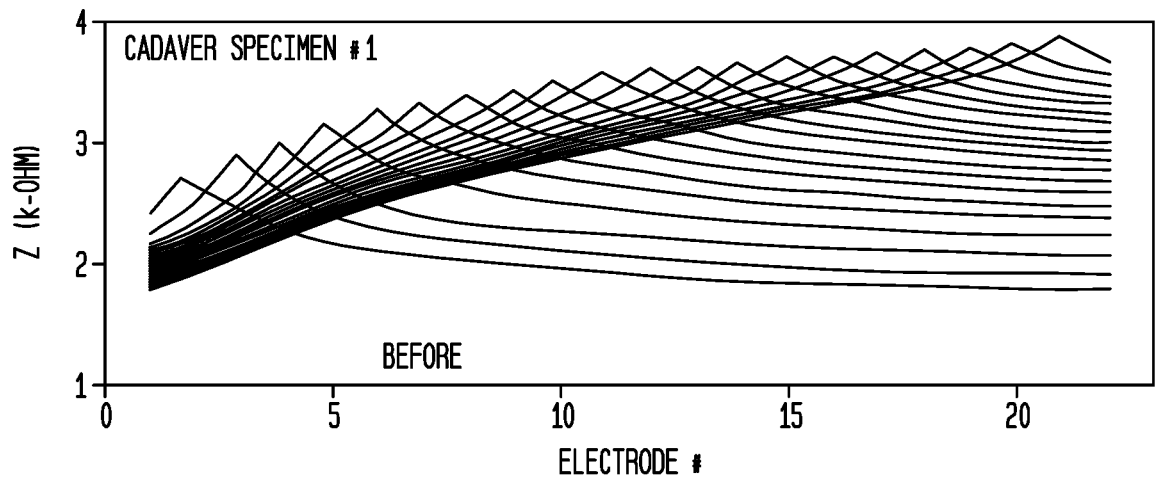
FIG. 4A is a diagram illustrating an example Electrode Voltage Tomography (EVT) curve obtained from a first cochlear cadaver specimen prior to insertion of an apical electrode therein, in accordance with certain embodiments presented herein.
Figure 4B:
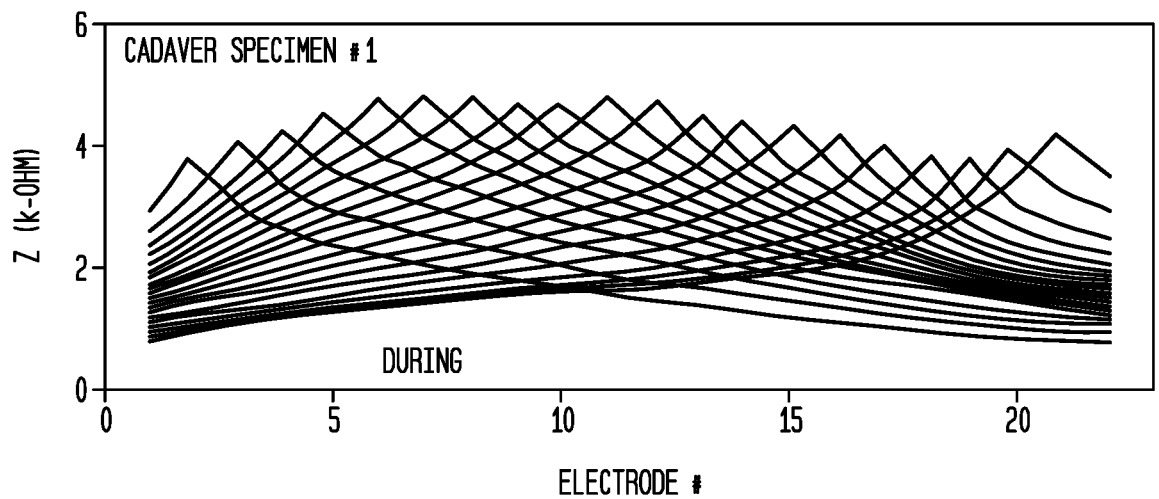
FIG. 4B is a diagram illustrating an example EVT curve obtained from a first cochlear cadaver specimen during insertion of an apical electrode therein, in accordance with certain embodiments presented herein.
Figure 4C:
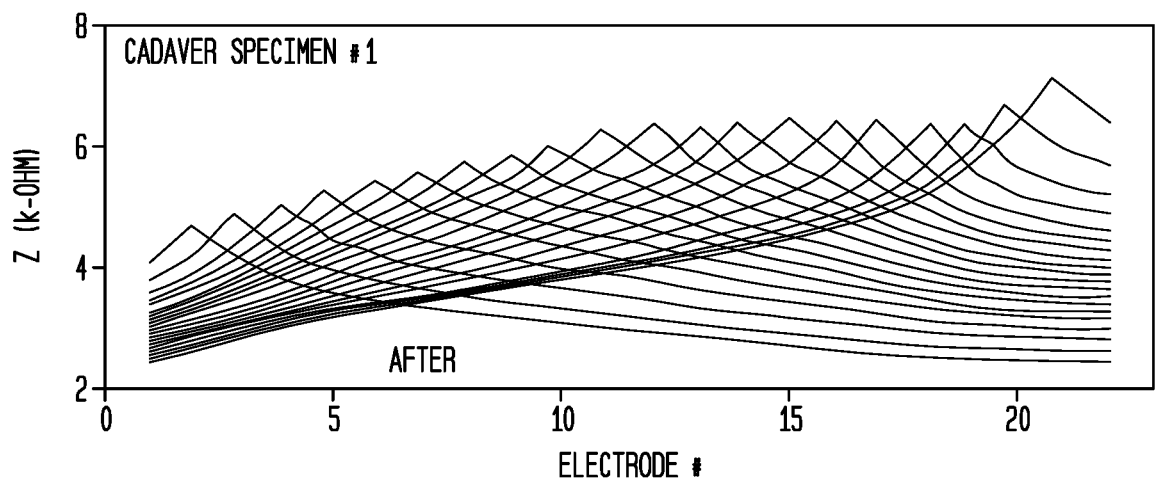
FIG. 4C is a diagram illustrating an example EVT curve obtained from a first cochlear cadaver specimen after removal of an apical electrode therefrom, in accordance with certain embodiments presented herein.
Figure 5A:
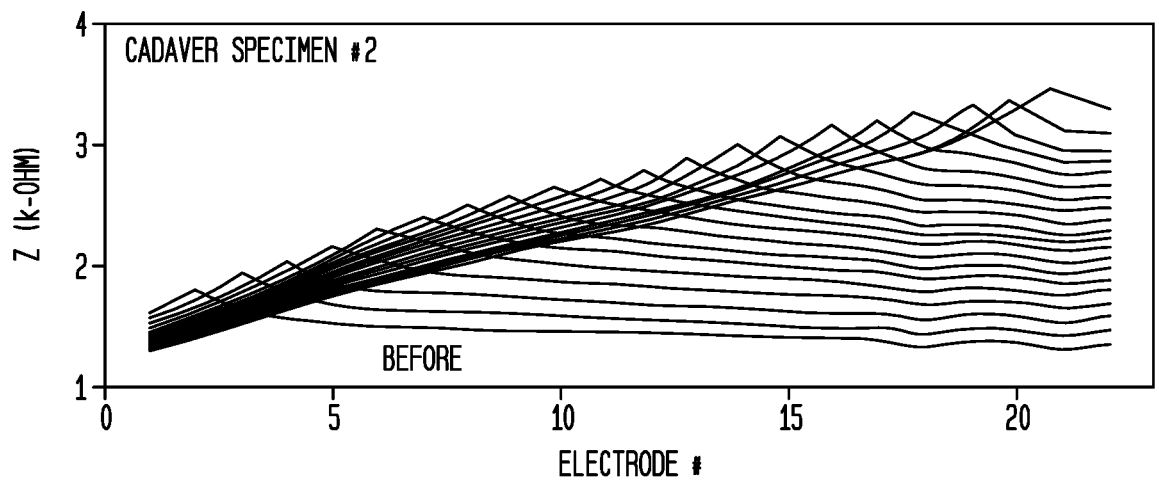
FIG. 5A is a diagram illustrating an example EVT curve obtained from a second cochlear cadaver specimen prior to insertion of an apical electrode therein, in accordance with certain embodiments presented herein.
Figure 5B:
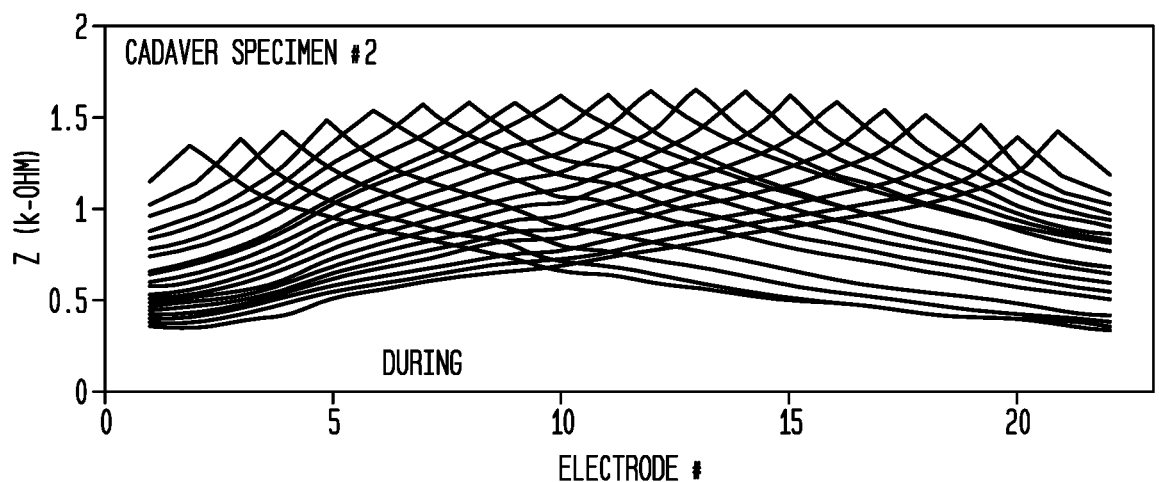
FIG. 5B is a diagram illustrating an example EVT curve obtained from a second cochlear cadaver specimen during insertion of an apical electrode therein, in accordance with certain embodiments presented herein.
Figure 5C:
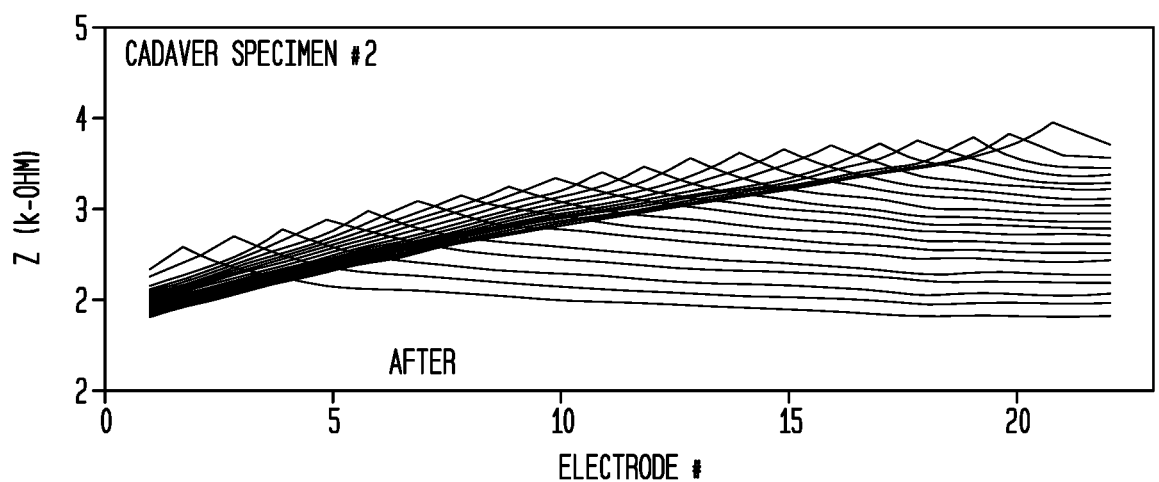
FIG. 5C is a diagram illustrating an example EVT curve obtained from a second cochlear cadaver specimen after removal of an apical electrode therefrom, in accordance with certain embodiments presented herein.

More specifically, FIGS. 4A and 4B illustrate example EVT curves obtained before insertion and during insertion, respectively, of an apical electrode into a first cochlear cadaver specimen, while FIG. 4C illustrates an example EVT curve obtained after the apical electrode is removed from the first cochlear cadaver. FIGS. 5A and 5B illustrate example EVT curves obtained before insertion and during insertion, respectively, of an apical electrode into a second cochlear cadaver specimen, while FIG. 5C illustrates an example EVT curve obtained after the apical electrode is removed from the second cochlear cadaver.

The EVT curves shown in FIGS. 4A-4C and 5A-5C are each obtained via a basilar cochlea electrode assembly comprising twenty-two (22) intra-cochlea electrodes inserted into the respective cochlear cadaver specimen. FIGS. 4B and 5B, in particular, illustrate that impedance decreases towards the apical end of the cochlea, which indicates there is an increased drop in voltage per distance compared to that which is shown in FIGS. 4A and 5A (and FIGS. 4C and 5C). The increased drop in voltage per distance is an indication that the apical electrode is in contact with the fluid and drawing current in that direction.

Figure 7:
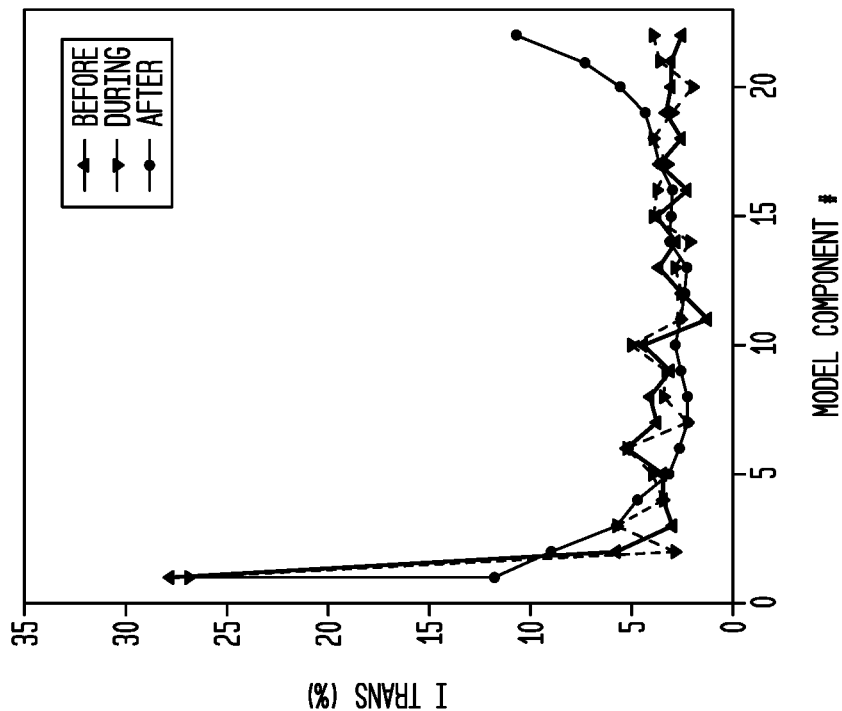
FIG. 7 is a graph illustrating the effect of opening a second cochlear cadaver specimen and placing an apical electrode at the apex thereof, in accordance with certain embodiments presented herein.
Figure 6:
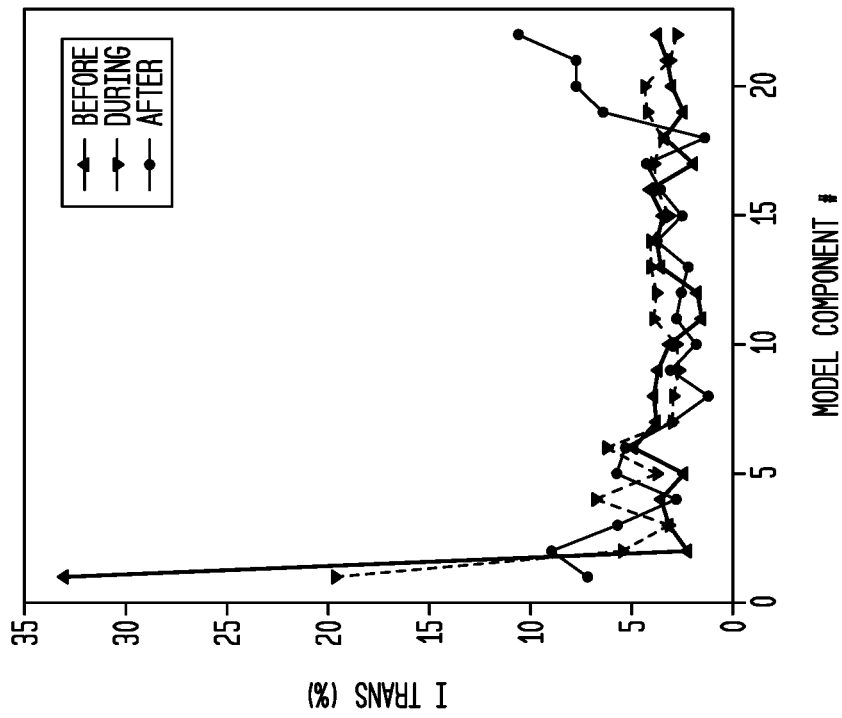
FIG. 6 is a graph illustrating the effect of opening a first cochlear cadaver specimen and placing an apical electrode at the apex thereof, in accordance with certain embodiments presented herein.

FIGS. 6 and 7 illustrate the effect of opening first and second cochlear cadaver specimens, respectively, and placing an apical electrode at the apex of the cochlea in terms of the percentage of current flowing out of the cochlea at each site. In FIGS. 6 and 7, ITrans (%) is the percent of transverse current exiting the cochlea at each cochlear location. The EVT measures were analyzed to derive the amount of current exiting the cochlea at each cochlear location.

FIGS. 6 and 7 each include includes three curves, where the first curve provides an indication of the current flow "before" placement of the apical electrode, the second provides an indication of the current flow "during" placement of the apical electrode (i.e., while the apical electrode is positioned in the apical region of the cochlea), and the third curve of provides an indication of the current flow "after" placement of the apical electrode (i.e., after the apical electrode has been removed/explanted from the cochlea).

As can be seen in FIGS. 6 and 7, the "before" and "after" curves are similar for both specimens. The "during" curves (i.e., when the apex was open and the apical electrode was placed inside it), reduced the current flow at component #1 and increased current flow at each of model components #19-#22. In these examples, the model components correspond to intra-cochlear electrodes, where model component #1 corresponds to the most proximal intra-cochlea electrode and model component #22 corresponds to the most apical intra-cochlea electrode. For specimen #2, the sealing of the cochlea was additionally secured using cyanoacrylate which may have been responsible for the greater similarity of the before and after results.

Figure 8A:
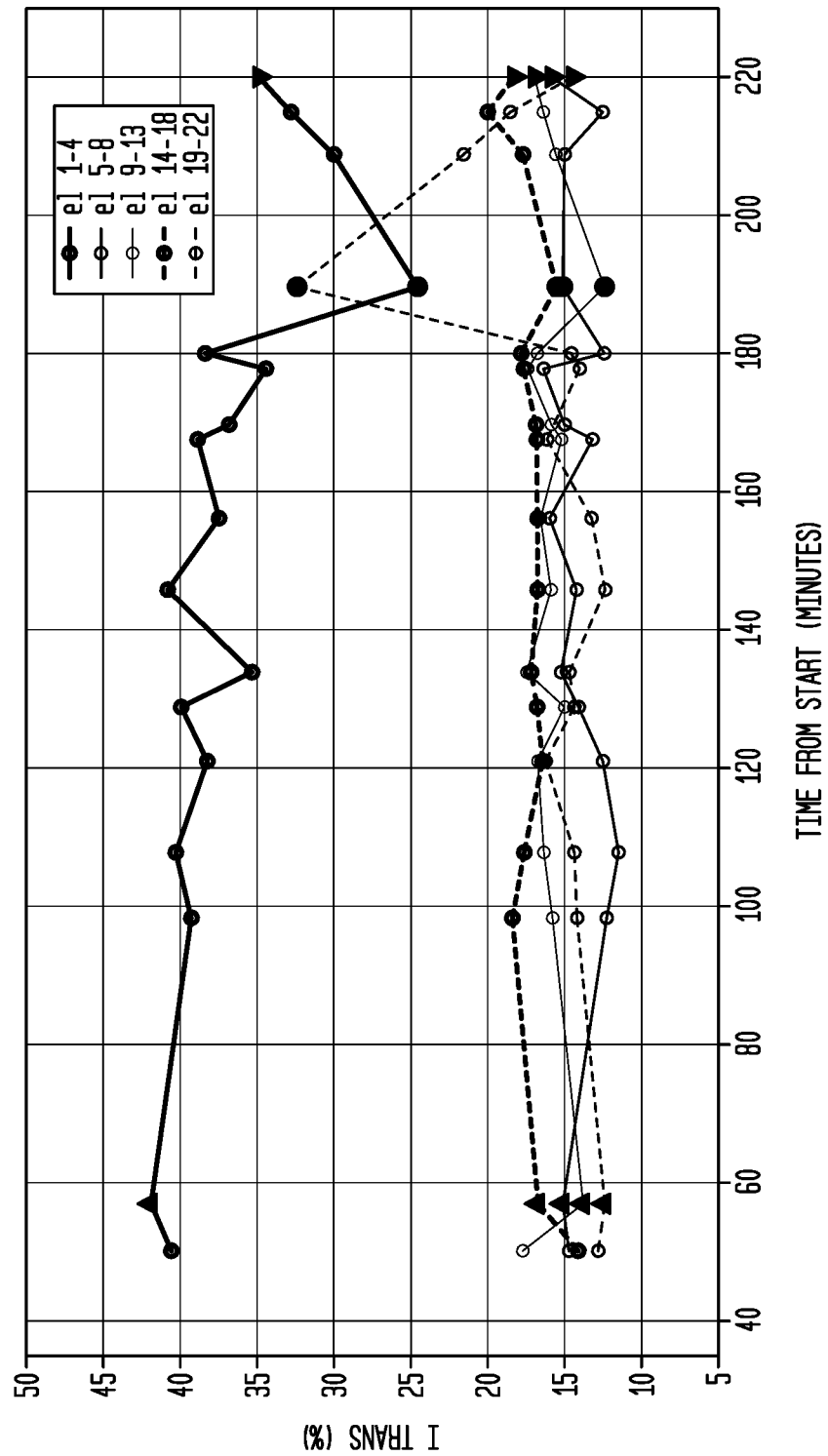
FIG. 8A is a graph illustrating Summed Transverse currents through groups of electrodes implanted in a first cochlear cadaver specimen, in accordance with certain embodiments presented herein.

FIGS. 8A and 8B illustrate Summed Transverse currents (ITrans (%)) through groups of 4 electrodes (el) (e.g., el 1 to 4, el 5 to 8, el 19 to 12) or 5 electrodes (e.g., el 9 to 13, el 14 to 18) over time for the first and second cadaver specimens of FIGS. 6 and 7, respectively. These FIGS. illustrate that the only sizeable change in apical/basal current flow occurred while the apical electrode was inserted into the cochlea (e.g., at approximately the 190 minute time). In addition, there is very little current flow change for electrodes 5 to 18. In FIGS. 8A and 8B, the upward arrow represents the "before" event, and the solid circle represents the "during" event, and the downward facing arrow represents the "after" event.

As noted above, the techniques presented herein may also use Neural Response Telemetry (NRT) measurements to determine whether apical electrode 154 is in electrical contact with the perilymphatic fluid space 109. For example, the neural responses will change their form in that there will be different amounts of masking between electrodes when the apical electrode 154 is in electrical contact with the perilymphatic fluid space 109. In one specific example, a resulting NRT spatial response profile (achieved by masking) can be measured and analyzed. The NRT spatial response profile should shift more apically and/or become narrower when a portion of current is drawn through the apical electrode 154. In addition, the apical electrode will create neural responses when it is placed. In other words, results of the NRT measurements may be used to determine a present spatial profile pattern in the cochlea 140 resulting from insertion of the apical electrode 154 through the opening in the inner ear (e.g., apical cochleostomy 156) and the determined spatial profile pattern may be compared to a predetermined spatial profile pattern. In certain examples, the predetermined spatial profile pattern is a spatial profile pattern determined using results of NRT measurements obtained prior to insertion of the apical electrode 154 through the apical cochleostomy 156.

In certain such embodiments, current can be delivered via apical electrode 154 and an extra-cochlear electrode, such as extra-cochlear electrode 153, can be used as the reference electrode (e.g., current return point). While this current is delivered, neural responses are measured at one or more of the intra-cochlear electrodes 162(1)-162(22). If the apical electrode 154 has a low-impedance path to the perilymphatic fluid space 109, the current delivered between the apical electrode 154 and the extra-cochlear electrode 153 will evoke a specific pattern of neural responses (e.g., different masking between electrodes) at some or all of the intra-cochlear electrodes 162(1)-162(22).

As noted above, FIG. 3 generally illustrates a method for assessing one outcome associated with implantation of an apical electrode into a cochlea of a recipient, namely determining when at least one apical electrode has a low-impedance path to the perilymphatic fluid space 109. It is to be appreciated that this specific assessment is one example and the techniques presented herein may be used to perform assessments of other outcomes associated with implantation of electrodes into the inner ear of a recipient.

Figure 9A:
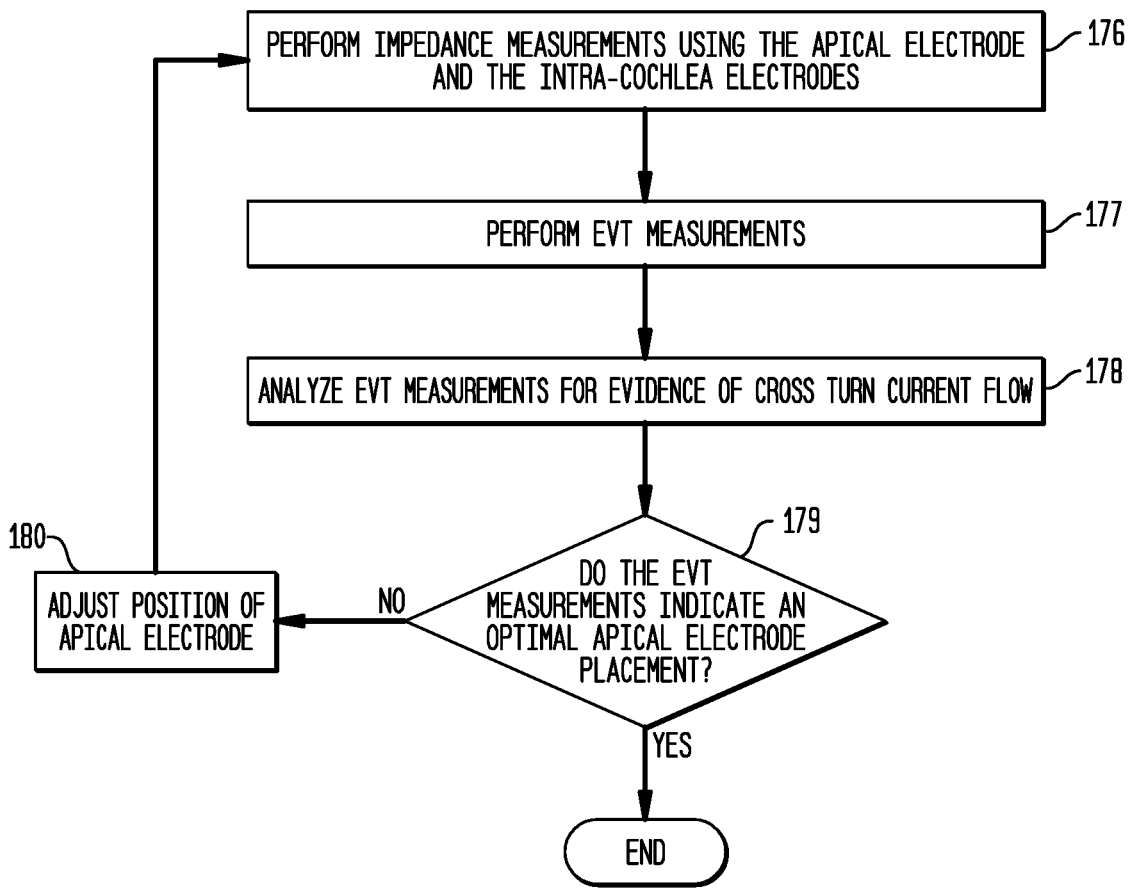
FIG. 9A is a flowchart illustrating a method, in accordance with certain embodiments presented herein.
Figure 9B:
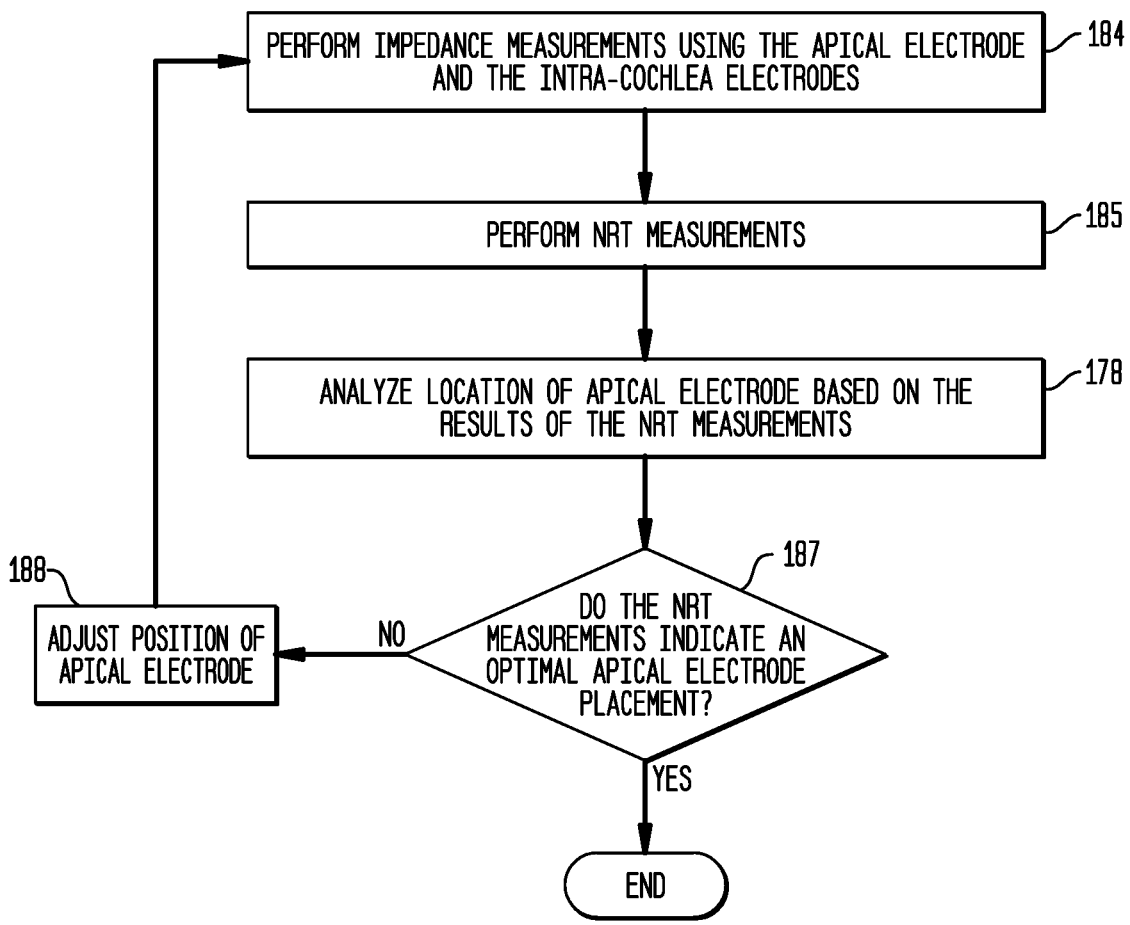
FIG. 9B is a flowchart illustrating a method, in accordance with certain embodiments presented herein.

More specifically, in accordance with certain embodiments, the techniques presented herein may alternatively or additionally used to determine an optimal location for one or more apical electrodes implanted in the apical region of a cochlea. For example, the techniques presented herein may use electrical stimulation and recording to determine the transimpedance matrix of the cochlea and adjust the apical electrode position to achieve the ideal location, such as a location minimizes cross-turn stimulation at the apex. FIGS. 9A and 9B are flowcharts illustrating further details for example techniques for determining an optimal location for one or more apical electrodes implanted in the apical region of a cochlea. For ease of illustration, FIGS. 9A and 9B will be described with reference to determining an optical location for apical electrode 154 in apical region 138 of cochlea 140, all described above with reference to FIG. 2. FIG. 9A illustrates a method that utilizes EVT measurements to determine the optimal location of the apical electrode 154, while FIG. 9B illustrates a method that utilizes NRT measurements to determine the optimal location of the apical electrode 154. The electrical measurements performed in FIGS. 9A and 9B are sometimes referred to herein as supplemental electrical measurements because, in certain embodiments, these measurements are performed after the apical electrode 154 is determined to be in electrical contact with the perilymphatic fluid space 109.

Referring first to FIG. 9A, shown is a method 175 that begins after apical electrode 154 is determined to be in electrical contact with the perilymphatic fluid space 109 (as described above with reference to FIG. 3). At 176, impedance measurements are performed between the apical electrode 154 and one or more of the intra-cochlea electrodes 162(1)-166(22) of basilar cochlea assembly 158. At 177, EVT measurements are performed.

In certain examples, the EVT measurements at 177 include a plurality of sequential measurement sets that each involve the delivery of current between the one of the intra-cochlea electrodes 162(1)-162(22) and extra-cochlear electrode 153. With each delivery of current between the one of the intra-cochlea electrodes 162(1)-162(22) and extra-cochlear electrode 153, voltages measurements between extra-cochlear electrode 153 and each of the other intra-cochlea electrodes 162(1)-162(22), as well as apical electrode 154, are obtained. For example, these EVT measurements may use an extra-cochlear electrode, such as extra-cochlear electrode 153, as both the stimulation and recording reference and use intra-cochlea electrodes 162(1)-162(22) and apical electrode 154 as active stimulating and active recording electrodes.

For example, one voltage measurement set includes the delivery of current between intra-cochlea electrode 162(1) and extra-cochlear electrode 153. In response, the voltages between extra-cochlear electrode 153 and each of the intra-cochlea electrodes 162(2)-162(22), as well as a voltage measurement between extra-cochlear electrode 153 and apical electrode 154, are measured. This process may be repeated for one or more (or all) of the other intra-cochlea electrodes as the current delivery electrode.

At 178, the apical electrode 154 the results of the EVT measurements are analyzed for evidence of cross turn current flow. In particular, the EVT measurements could demonstrate a pattern of response indicating proper placement, such as monotonically decreasing magnitudes from apex to base could indicate no cross turn stimulation.

At 179, based on the analysis at 178, a determination is made as to whether the EVT measurements indicate an optimal apical electrode placement. As noted, this determination may be whether an acceptable amount of cross turn current flow (e.g., no cross turn current flow and/or the cross turn is below a threshold level) is identified or also for instance the response pattern indicates a single punctate area of activation.

If it is determined at 179 that the EVT measurements indicate an optimal apical electrode placement (e.g., there is an acceptable amount of cross turn current flow), then method 175 may end. However, if that the EVT measurements indicate that the apical electrode 156 is not in an optimal location (e.g., significant cross turn current flow is present), then the position of the apical electrode 154 is adjusted at 180. The operations at 176, 177, 178, 179, and 180 may be repeated until an optimal apical electrode placement is achieved (e.g., until only an acceptable amount of cross turn current flow is present).

As noted above, FIG. 9B illustrates a method 183 that utilizes NRT measurements to determine the optimal location of the apical electrode 154. Method 183 that begins after apical electrode 154 is determined to be in electrical contact with the perilymphatic fluid space 109 (as described above with reference to FIG. 3). At 184, impedance measurements are performed between the apical electrode 154 and one or more of the intra-cochlea electrodes 162(1)-166(22) of basilar cochlea assembly 158. At 185, NRT measurements are performed. At 186, the location of the apical electrode 154 is analyzed using the results of the NRT measurements. In certain embodiments, the magnitude of the neural response to stimulation via apical electrode 154 as masker and probe is examined.

The analysis at 186 may take a number of different forms. In one example, the NRT measurements on a variety of the intra-cochlea electrodes 162(1)-166(22) of basilar cochlea assembly 158 should demonstrate a pattern of response indicating proper placement. That is, monotonically decreasing magnitudes from apex to base could indicate the neural stimulation is of low-frequency auditory nerve fibers. In another example, spread of excitation measures should determine if the location of apical electrode 154 minimizes interaction between the apical electrode and other one or more of the intra-cochlea electrodes 162(1)-166(22). In a still other example, an NRT spatial response profile (achieved by masking) should shift more apically and/or become narrower when a portion of current is drawn through the apical electrode 154. This may be a useful tool, for example, to assess the best location intraoperatively for certain uses of the approach. The spatial shift in neural response peak could be a useful indicator of correct apical electrode position intraoperatively.

Returning to FIG. 9B, based on the analysis at 186, a determination is made at 187 whether the NRT measurements indicate an optimal apical electrode placement (e.g., in one of the manners described above). If it is determined at 187 that the NRT measurements indicate an optimal apical electrode placement, then method 183 ends. However, if that the NRT measurements indicate that the apical electrode 156 is not in an optimal location, then the position of the apical electrode 154 is adjusted at 188. The operations at 184, 185, 186, 187, and 188 may be repeated until an optimal apical electrode placement is achieved.

As noted above, FIG. 3, FIG. 9A, and FIG. 9B illustrate methods for assessing specific outcomes associated with implantation of an apical electrode into a cochlea of a recipient. FIG. 10 is a flowchart illustrating a method 190 for assessing another outcome associated with implantation of electrodes into the inner ear of a recipient, namely to confirm electrically sealing of an opening through which an electrode is implanted into a recipient's inner ear. Merely for ease of illustration, method 190 will be described with reference to confirming the seal of apical cochleostomy 156 after insertion of apical electrode 154 into apical region 138 of cochlea 140, described above with reference to FIG. 2.

Method 190 generally makes use of electrical measurements, such as impedance measurements, to confirm the apical cochleostomy 156 is sealed. More specifically, method 190 begins at 191 where, following implantation of apical electrode 154 into the cochlea 140, one or more initial electrical measurements are performed between the apical electrode 154 (within the cochlea 140) and an extra-cochlear electrode that is external to (i.e., outside) of the cochlea 140. The results of the one or more initial electrical measurement are then recorded. In certain embodiments, the one or more initial electrical measurement may be impedance measurements to capture the impedance between the apical electrode 154 and the extra-cochlear electrode. The extra-cochlear electrode may be, for example, the extra-cochlear electrode 153 or other electrode located outside of the cochlea.

At 192, the apical cochleostomy 156 is sealed using a bone pate or other standard technique. At 193, one or more additional electrical measurements are performed between the apical electrode 154 (within the cochlea 140) and the extra-cochlear electrode and the results of the one or more additional electrical measurements are then recorded. In certain embodiments, the one or more additional electrical measurements is an impedance measurement to capture the impedance between the apical electrode 154 and the extra-cochlear electrode. Again, in certain embodiments, the one or more additional may be impedance measurements to capture the impedance between the apical electrode 154 and the extra-cochlear electrode.

At 194, the results of the one or more initial electrical measurements and/or the results of the one or more additional electrical measurement are analyzed to determine whether the apical cochleostomy 156 is "electrically sealed." As used here, "electrically sealed" refers to a seal that forms a sufficiently high impedance barrier (e.g., significantly greater than 1 k-ohm) between the apical electrode 154 and the extra-cochlear environment. In certain embodiments in which the one or more initial electrical measurements and the one or more additional electrical measurements are impedance measurements, the analysis at 179 may comprise an analysis of the relative change in the measured impedances.

In other embodiments in which the one or more initial electrical measurements and the one or more additional electrical measurements are impedance measurements, the analysis at 194 may comprise a determination of whether the impedance measured after sealing of the apical cochleostomy 156 is similar to the a level associated with bone resistivity. In certain such embodiments, the one or more initial electrical measurements may be omitted.

Figure 11:
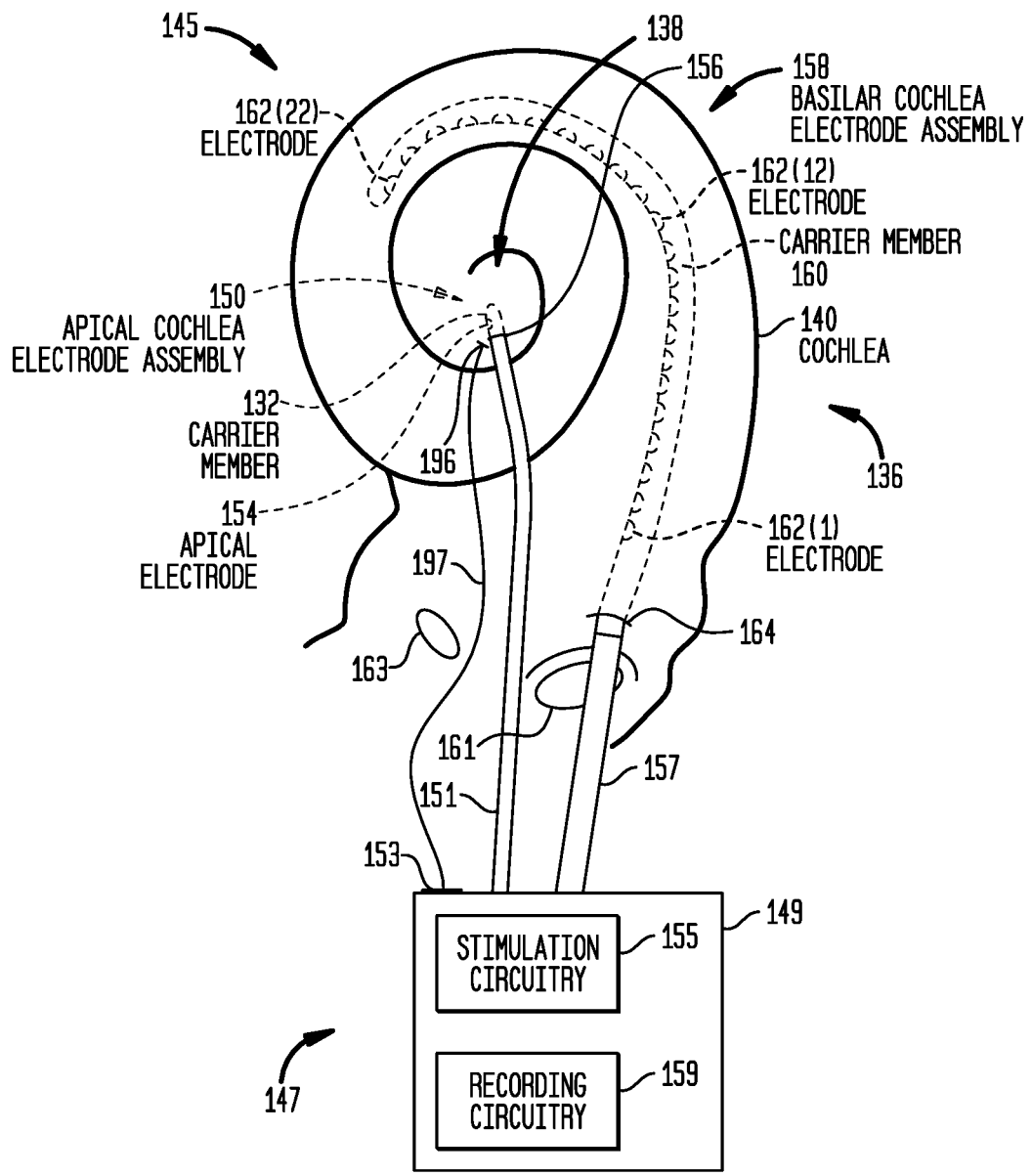
FIG. 11 is a schematic diagram illustrating an apical cochlea electrode assembly and a basilar cochlea electrode assembly implanted in a cochlea of a recipient, in accordance with certain embodiments presented herein.

As noted, in the embodiment of FIG. 10, electrical measurements (e.g., impedance measurements) are performed between the apical electrode 154 and an extra-cochlear electrode. In certain embodiments, the extra-cochlear electrode is electrode 153, described above with reference to FIG. 2, which is disposed on the outer housing (can) 149 of the implanted stimulation unit 147. In another embodiment, the extra-cochlear electrode is an electrode disposed adjacent to apical cochleostomy 156 and connected to the electrode 153 via a wire. FIG. 11 illustrates an example of such an arrangement.

More specifically, FIG. 11 illustrates an arrangement that is similar to that shown in FIG. 2. However, FIG. 11 also illustrates that an extra-cochlear electrode 196 is positioned on the outer surface of cochlea 140 at a location adjacent to the apical cochleostomy 156. The extra-cochlear electrode 196 is electrically connected to electrode 153 via a wire 197.

FIG. 12 is a block diagram of a fitting system 288 for use with certain aspects of the techniques presented herein. Fitting system 288 is, in general, a computing device that comprises a plurality of interfaces/ports 289(1)-289(N), a memory 290, a processor 291, a user interface 292, and a display screen 293. The interfaces 289(1)-289(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 12, interface 289(1) is connected to cochlear implant 145 (FIG. 2) implanted in a recipient 294.

Interface 289(1) may be directly connected to the cochlear implant 145 or connected to a device (e.g., remote control device, behind-the-ear processor, etc.) that is communication with the cochlear implant 145. Interfaces 289(1)-289(N), may be configured to transmit/receive signals via a wired or wireless connection (e.g., telemetry, Bluetooth, etc.).

Memory 290 comprises electrode implantation assessment logic 295. Memory 290 may comprise any one or more of read only memory (ROM), random access memory (RAM), magnetic disk storage media devices, optical storage media devices, flash memory devices, electrical, optical, or other physical/tangible memory storage devices. The processor 291 is, for example, a microprocessor or microcontroller that executes instructions for the electrode implantation assessment logic 295. Thus, in general, the memory 290 may comprise one or more tangible (non-transitory) computer readable storage media (e.g., a memory device) encoded with software comprising computer executable instructions and when the software is executed (by the processor 291) it is operable to perform the operations described herein in connection with the assessment of outcomes associated with implantation of one or more electrodes into the inner ear of a recipient.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
    forming at least a portion of a hole in an apical region of an inner ear of a recipient;
    positioning at least one electrode of a first electrode assembly at the at least the portion of the hole in the apical region of the inner ear of the recipient;
    performing one or more electrical measurements via electrodes of a second electrode assembly implanted in, or in proximity to, the inner ear; and
    analyzing data obtained as a result of the one or more electrical measurements performed via the electrodes of the second electrode assembly to determine whether the at least one electrode of the first electrode assembly has a low-impedance path to a perilymphatic fluid space of the inner ear.

2. The method of claim 1, wherein positioning the at least one electrode at the at least the portion of the hole in the apical region of the inner ear of the recipient comprises:
    inserting the at least one electrode into the inner ear.

3. The method of claim 2, further comprising:
    performing the one or more electrical measurements during insertion of the at least one electrode into the inner ear; and
    terminating insertion of the at least one electrode upon a determination that the at least one electrode has a low-impedance path to the perilymphatic fluid space.

4. The method of claim 2, wherein following insertion of the at least one electrode, the method further comprises:

performing supplemental electrical measurements via electrodes implanted in, or in proximity to, the inner ear; and based on data obtained as a result of the supplemental electrical measurements, evaluating an implanted location of the at least one electrode.

5. The method of claim 4, further comprising:

based on the evaluating adjusting the implanted location of the at least one electrode.

6. The method of claim 1, wherein analyzing data obtained as a result of the one or more electrical measurements to determine whether the at least one electrode has a low-impedance path to the perilymphatic fluid space comprises:

analyzing the data obtained from the one or more electrical measurements to determine when the at least one electrode is in physical contact with perilymph of the inner ear.

7. The method of claim 1, wherein analyzing data obtained as a result of the one or more electrical measurements to determine whether the at least one electrode has a low-impedance path to the perilymphatic fluid space comprises:

analyzing the data obtained from the one or more electrical measurements to determine when the at least one electrode is in physical contact with an endosteum of the inner ear.

8. The method of claim 1, further comprising:

inserting one or more electrodes into a basal region of inner ear.

9. The method of claim 8, wherein performing one or more electrical measurements via electrodes implanted in, or in proximity to, the inner ear comprises:

performing one or more electrical measurements using at least one of the one or more electrodes or the at least one electrode.

10. The method of claim 1, wherein performing one or more electrical measurements via electrodes implanted in, or in proximity to, the inner ear comprises:

delivering current signals to the inner ear via one or more of the electrodes implanted in, or in proximity to, the inner ear; and performing one or more voltage or impedance measurements via at least one of the electrodes implanted in, or in proximity to, the inner ear.

11. The method of claim 10, wherein analyzing data obtained as a result of the one or more electrical measurements to determine whether the at least one electrode has a low-impedance path to the perilymphatic fluid space comprises:

using data obtained as a result of the one or more voltage or impedance measurements to determine a selected pattern of current flow in the inner ear towards an apex of the inner ear.

12. The method of claim 11, wherein the selected pattern of current is an increased flow of current towards the apex of the inner ear relative to a pattern of current flow determined using results of one or more voltage or impedance measurements obtained prior to positioning of the at least one electrode.

13. The method of claim 1, wherein performing one or more electrical measurements via electrodes implanted in, or in proximity to, the inner ear comprises:

performing Electrode Voltage Tomography (EVT) measurements via at least one of the electrodes implanted in, or in proximity to, the inner ear.

14. The method of claim 1, wherein performing one or more electrical measurements via electrodes implanted in, or in proximity to, the inner ear comprises:

delivering current signals to the inner ear via one or more of the electrodes implanted in, or in proximity to, the inner ear; and performing neural response telemetry (NRT) measurements via at least one of the electrodes implanted in, or in proximity to, the inner ear.

15. The method of claim 14, wherein analyzing data obtained as a result of the one or more electrical measurements to determine whether the at least one electrode has a low-impedance path to the perilymphatic fluid space comprises:

using data obtained as a result of the NRT measurements to determine a present spatial profile pattern in the inner ear resulting from positioning of the at least one electrode; and comparing the present spatial profile pattern in the inner ear to a predetermined spatial profile pattern.

16. The method of claim 15, wherein the predetermined spatial profile pattern is a spatial profile pattern determined using results of NRT measurements obtained prior to positioning of the at least one electrode.

17. A method, comprising:

inserting a first component into a basal region of an inner ear of a recipient;

forming at least a portion of a hole at an apical region of the inner ear;

inserting a second component into the at least the portion of the hole formed at the apical region of the inner ear;

delivering a first therapy to the inner ear via the first component; and delivering a second therapy to the inner ear via the second component.

18. The method of claim 17, wherein the first component is a plurality of electrodes, and wherein delivering a first therapy to the inner ear via the first component comprises:

delivering current signals to the inner ear using one or more of the plurality of electrodes.

19. The method of claim 17, wherein the second component comprises one or more apical electrodes, and wherein delivering a second therapy to the inner ear via the second component comprises:

delivering current signals to the inner ear using at least one of the one or more apical electrodes.

20. The method of claim 17, further comprising:

performing one or more electrical measurements via electrodes implanted in, or in proximity to, the inner ear; and analyzing data obtained as a result of the one or more electrical measurements to determine whether the second component has a low-impedance path to a perilymphatic fluid space of the inner ear.

21. The method of claim 20, wherein performing one or more electrical measurements via electrodes implanted in, or in proximity to, the inner ear comprises:

performing one or more electrical measurements using one or more of a plurality of electrodes inserted into a basal region of the inner ear or at least one apical electrode inserted into an apical region of the inner ear.

* * * * *